US012797634B2

(12) United States Patent
Kim et al.

(10) Patent No.: US 12,797,634 B2
(45) Date of Patent: Nov. 17, 2026

(54) BODY-CUSTOMIZED LIGHT IRRADIATION APPARATUS AND METHOD FOR CONTROLLING SAME

(71) Applicant: WONTECH Co., Ltd., Daejeon (KR)

(72) Inventors: Jong Won Kim, Seongnam-si (KR); Jung Hyun Kim, Seongnam-si (KR); Young Seok Seo, Sejong-si (KR); Chang Woo Lee, Daejeon (KR)

(73) Assignee: WONTECH Co., Ltd., Daejeon (KR)

( * ) Notice: Subject to any disclaimer, the term of this patent is extended or adjusted under 35 U.S.C. 154(b) by 391 days.

(21) Appl. No.: 18/050,957

(22) Filed: Oct. 28, 2022

(65) Prior Publication Data

US 2024/0139539 A1 May 2, 2024

(30) Foreign Application Priority Data

Oct. 26, 2022 (KR) ........................ 10-2022-0139211

(51) Int. Cl.
*A61N 5/06* (2006.01)
*A61N 5/067* (2006.01)

(52) U.S. Cl.
CPC .... *A61N 5/0617* (2013.01); *A61N 2005/0642* (2013.01); *A61N 2005/0647* (2013.01); *A61N 2005/0651* (2013.01); *A61N 2005/0663* (2013.01); *A61N 5/067* (2021.08)

(58) Field of Classification Search
CPC ............ A61N 2005/0642; A61N 5/067; A61N 2005/0647; A61N 5/0617; A61N 2005/0651; A61N 2005/0663; A61N 2005/0643; A61N 2005/065; A61N 2005/0662; A61N 2005/0626; A61N 2005/0632; A61N 2005/0652
See application file for complete search history.

(56) References Cited

U.S. PATENT DOCUMENTS

2017/0340897 A1* 11/2017 Unger .................. A61N 5/0617
2018/0117355 A1* 5/2018 Loupis ................. A61N 5/0616
2020/0405163 A1* 12/2020 Hilgers ................ A61B 5/0295
2021/0379388 A1* 12/2021 Connor ............... A61M 60/531
2022/0203117 A1* 6/2022 Wasserbauer ........ A61N 5/0617

FOREIGN PATENT DOCUMENTS

EP 2368599 A1 * 9/2011 ........... A61N 5/0617
KR 10-2013-0119164 A 10/2013
KR 10-2017-0093650 A 8/2017
KR 20170093650 A * 8/2017 ........... A61N 5/0617
WO WO-2009086452 A1 * 7/2009 ............ H01H 13/78

* cited by examiner

*Primary Examiner* — Lynsey C Eiseman
*Assistant Examiner* — Benjamin Allyn Schmitt
(74) *Attorney, Agent, or Firm* — Harvest IP Law, LLP

(57) ABSTRACT

The present invention relates to a light irradiation apparatus including: a body part, base parts coupled to the body part, light irradiators coupled to the corresponding base part to irradiate light on a user's body, and position adjustors for adjusting the light irradiators in position and having one or more actuators controlled by a computing device, wherein the one or more actuators adjust the light irradiators in position so that the positions of the light irradiators correspond to the user's body on which the light is irradiated.

13 Claims, 18 Drawing Sheets

(a) (b)

(a)

(b)

(a) Basic Mode (b) Mode for top of the head (a)Initial Position (b)Contact (Sensor Detection)

(c)Distance Adjustment

BODY-CUSTOMIZED LIGHT IRRADIATION APPARATUS AND METHOD FOR CONTROLLING SAME

CROSS REFERENCE TO RELATED APPLICATION OF THE INVENTION

The present application claims the benefit of Korean Patent Application No. 10-2022-0139211 filed in the Korean Intellectual Property Office on Oct. 26, 2022, the entire contents of which are incorporated herein by reference.

FIELD OF THE INVENTION

The present invention relates to a body-customized light irradiation apparatus and a method for controlling the same, and more specifically, to a light irradiation apparatus and a method for controlling the same that are capable of allowing light to be irradiated customizedly to a human or animal body shape.

BACKGROUND OF THE RELATED ART

Hair grows out of the epidermis so that the hair has a cycle and a metabolism. Each hair has the hair cycle consisting of a new birth phase, a growth phase, a regression phase, and a loss phase, and if a person is healthy, his or her hair cycle can last an average of 5 to 6 years. An adult has about one hundred thousands of hairs and normally loses around 80 hairs per day. If a greater number of hairs than 80 hairs per day are lost, he or she has alopecia.

To treat the alopecia, various technologies including a chemical therapy have been suggested, and recently, it is known that if beams with specific wavelengths are irradiated on body tissues, the metabolism on the corresponding region is boosted and the functions of the body tissues are activated, which is suggested as a Low Level Laser Therapy (LLLT) and applied to an alopecia treatment.

The LLLT makes use of the laser beams having wavelengths between 600 nm and 1300 nm and energy intensity between 1 mW and 1000 mW, and if the laser beams are irradiated on a user's scalp, the hair follicles and the living tissues around the hair follicles may be activated to expect hair re-growth promotion, hair growth promotion, and hair loss prevention.

So as to optimize the effectiveness of the LLLT, the laser beams with appropriate intensity have to be irradiated on positions where a treatment is needed. However, generally, the human scalp is curvedly or irregularly shaped, and further, the scalp is covered with hairs, so that it is hard to irradiate the laser beams with appropriate intensity on accurate positions of the scalp.

SUMMARY OF THE INVENTION

Accordingly, the present invention has been made in view of the above-mentioned problems occurring in the related art, and it is an object of the present invention to provide a body-customized light irradiation apparatus and a method for controlling the same that are capable of allowing light to be irradiated customizedly to a user's body, thereby optimizing treatment effectiveness.

It is another object of the present invention to provide a body-customized light irradiation apparatus and a method for controlling the same that are capable of allowing the light to be irradiated on a user's body to be adjusted in position and at angle even though the user's body is curvedly or irregularly shaped.

It is yet another object of the present invention to provide a body-customized light irradiation apparatus and a method for controlling the same that are capable of allowing the light to be irradiated on a user's body to be adjusted in distance to thus irradiate the light with optimal intensity on given positions of the user's body.

According to and embodiment of the present invention, there is provided a light irradiation apparatus comprising: a body part, base parts coupled to the body part, light irradiators coupled to the corresponding base part to irradiate light on a user's body, and position adjustors for adjusting the light irradiators in position and having one or more actuators controlled by a computing device, wherein the one or more actuators adjust the light irradiators in position so that the positions of the light irradiators correspond to the user's body on which the light is irradiated.

According to and embodiment of the present invention, a method for controlling a light irradiation apparatus, comprising the steps of: fixing a body part to a user's body, tilting base parts coupled to the body part toward at least portions of the user's body, adjusting light irradiators coupled to the corresponding base part in position, and irradiating light on the at least portions of the user's body from the light irradiators, wherein the step of adjusting the light irradiators in position is performed so that the positions of the light irradiators correspond to the at least portions of the user's body on which the light is irradiated.

BRIEF DESCRIPTION OF THE DRAWINGS

The above and other objects, features and advantages of the present invention will be apparent from the following detailed description of the embodiments of the invention in conjunction with the accompanying drawings, in which.

DETAILED DESCRIPTION OF THE EMBODIMENTS

Figure 1:
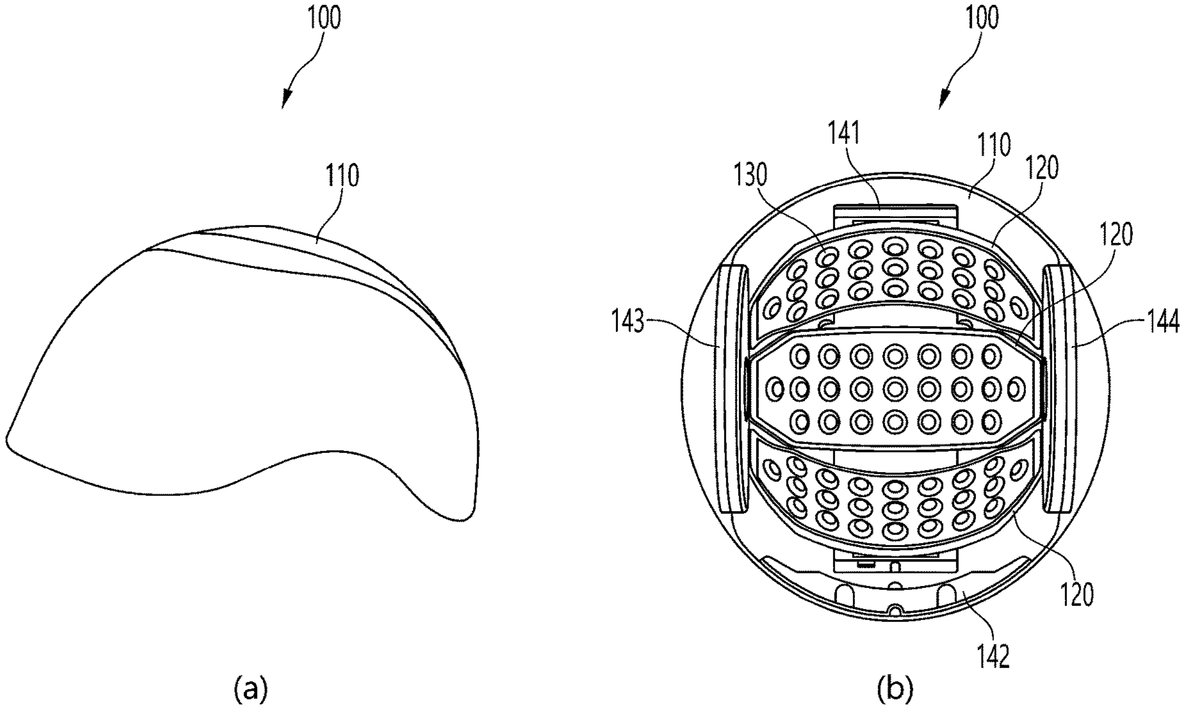
FIG. 1 shows a body-customized light irradiation apparatus according to the present invention.

Hereinafter, an explanation of embodiments of the present invention will be given in detail with reference to the attached drawings. Objects, characteristics and advantages of the present invention will be more clearly understood from the detailed description as will be described below and the attached drawings. Before the present invention is disclosed and described, it is to be understood that the disclosed embodiments are merely exemplary of the invention, which can be embodied in various forms. Those skilled in the art will envision many other possible variations within the scope of the present invention.

In the description, the corresponding parts in the embodiments of the present invention are indicated by corresponding reference numerals and the repeated explanation on the corresponding parts will be avoided. If it is determined that the detailed explanation on the well known technology related to the present invention makes the scope of the present invention not clear, the explanation will be avoided for the brevity of the description.

All terms used herein, including technical or scientific terms, unless otherwise defined, have the same meanings which are typically understood by those having ordinary skill in the art. The terms, such as ones defined in common dictionaries, should be interpreted as having the same meanings as terms in the context of pertinent technology, and should not be interpreted as having ideal or excessively formal meanings unless clearly defined in the specification. Terms used in this application are used to only describe specific exemplary embodiments and are not intended to restrict the present invention. An expression referencing a singular value additionally refers to a corresponding expression of the plural number, unless explicitly limited otherwise by the context.

Terms, such as the first, the second, A, B, (a), and (b) may be used to describe various elements, but the elements should not be restricted by the terms. The terms are used to only distinguish one element from the other element. When it is said that one element is described as being "connected" or "coupled" to the other element, one element may be directly connected or coupled to the other element, but it should be understood that another element may be present between the two elements.

Hereinafter, an explanation of embodiments of the present invention will be given in detail with reference to the attached drawings.

FIG. 1 shows a body-customized light irradiation apparatus according to the present invention. FIG. 1(*a*) is a side view showing an outer appearance of the body-customized light irradiation apparatus 100, and FIG. 1(*b*) is a bottom view showing principal parts of the body-customized light irradiation apparatus 100.

Referring to FIG. 1, the light irradiation apparatus 100 according to the present invention includes a body part 110, one or more base parts 120, a plurality of light irradiators 130, and/or a plurality of fixing parts 141, 142, 143, and 144.

The body part 110 serves as a housing in which the principal parts of the light irradiation apparatus 100 are protectedly accommodated. The outer appearance of the light irradiation apparatus 100 as shown in FIG. 1A is provided. According to the embodiment of the present invention, the body part 110 has the shape of a helmet, but it may not be limited necessarily thereto.

For example, if the light irradiation apparatus 100 is available to apply stimulations to a user's scalp, it may have the shape of a helmet. Contrarily, if the light irradiation apparatus 100 is available to apply stimulations to the user's face, it may have the shape of a face mask. Like this, the light irradiation apparatus 100 may have various shapes according to the user's body regions to which it is available.

The base parts 120 are coupled to the body part 110 to locate the plurality of light irradiators 130 on the surfaces thereof. The base parts 120 are adjustable in position and/or at angle by means of an actuator controlled by a computing device so as to allow the light emitted from the light irradiators 130 to be irradiated on the user's body at optimal angles and strength (intensity). As shown in FIG. 1(*b*), the base parts 120 are controlled in position and/or at angle, independently of one another. An explanation of the specific operations of adjusting the positions and/or angles of the base parts 120 will be given later with reference to FIG. 3.

The light irradiators 130 serve to irradiate the light with a predetermined wavelength range for the purpose of body stimulation, such as a low level laser therapy, and the like.

According to the embodiment of the present invention, the predetermined wavelength range is between 620 nm and 660 nm, and an amount of light outputted in the predetermined wavelength range is between 1.5 mW and 5.5 mW. Without being limited thereto, however, the predetermined wavelength range may be less than 620 nm or greater than 660 nm, and an amount of light outputted in the predetermined wavelength range may be less than 1.5 mW and greater than 5.5 mW.

According to the embodiment of the present invention, the light irradiators 130 may be laser diodes (hereinafter, referred to as LDs) or light emitting diodes (hereinafter, referred to as LEDs). In this case, the LDs and LEDs as the light irradiators 130 in one light irradiation apparatus 100 may be used together.

The fixing parts 141, 142, 143, and 144 serve to fix the light irradiation apparatus 100 to the user's body. The fixing parts 141, 142, 143, and 144 are disposed inside the light irradiation apparatus 100 and come into close contact with the user's body. As shown in FIG. 1(*b*), the fixing parts 141, 142, 143, and 144 are disposed at the front, back, and sides of the interior of the light irradiation apparatus 100, but they may be freely disposed inside the light irradiation apparatus 100, without being limited thereto. For example, the light irradiation apparatus 100 may have five or more fixing parts, and the fixing parts may be disposed equally spaced apart from one another along the inner periphery of the light irradiation apparatus 100.

The light irradiation apparatus 100 of the present invention is configured to allow the light irradiators 130 to be automatically adjusted in position so that the light irradiated from the light irradiators 130 corresponds to the user's body on which the light is irradiated. This means that the base parts 120 are adjusted at angle and/or in position or the light irradiators 130 are adjusted in position appropriately according to the shape or position of the user's body, so that the light irradiation angles or distances of the light irradiators 130 can be adjusted appropriately according to the shape or position of the user's body. An explanation of configurations and operating methods related to the adjustment of the base parts 120 and the light irradiators 130 will be given in detail with reference to FIG. 2.

Figure 2:
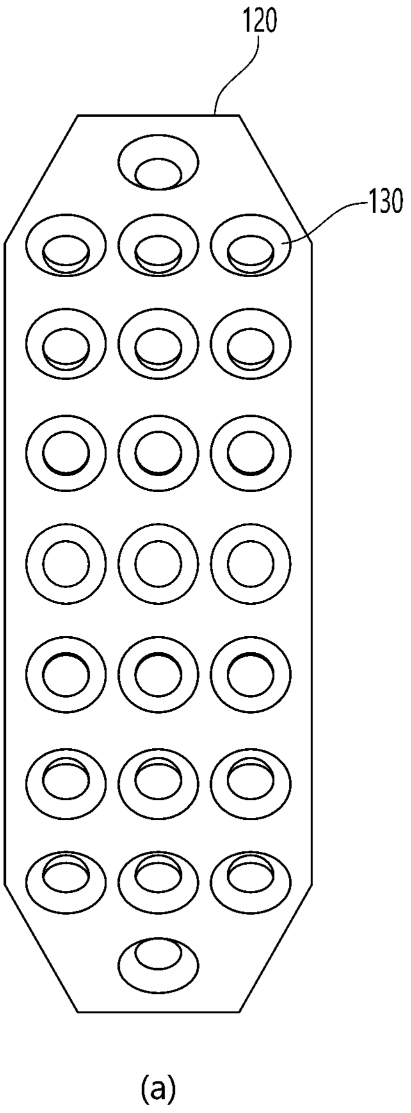
FIG. 2 shows a base part of FIG. 1.
Figure 2:
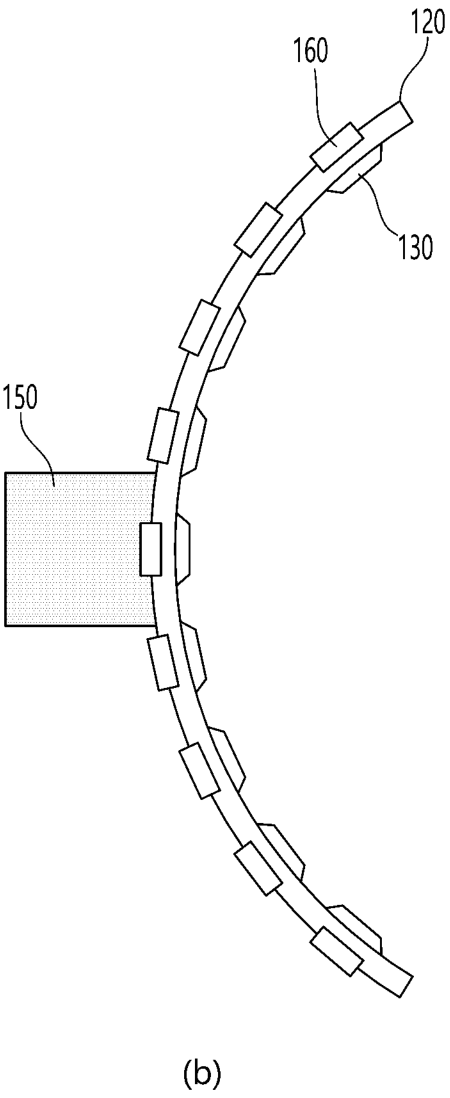

FIG. 2 shows the base part of FIG. 1. FIG. 2(*a*) is a top view showing one base part 120 and FIG. 2(*b*) is a side view showing the base part 120.

The base parts 120 are configured to locate the light irradiators 130 thereon. Each light irradiator 130 is attached to the surface of the corresponding base part 120, and otherwise, it may be built in the corresponding base part 120.

As shown in FIG. 2(*a*), the plurality of light irradiators 130 are arranged in rows and columns on the corresponding base part 120, but they may be differently arranged on the base part 120, without being limited thereto. For example, the plurality of light irradiators 130 may be arranged at given intervals along the circumference of the corresponding base part 120.

Further, each base part 120 has one or more actuators 150 and 160 coupled thereto or included therein as position adjustors for adjusting the base part 120 or the light irradiators 130 at angle or in position. One or more actuators 150 and 160 are controlled by the computing device and provide mechanical mechanisms for adjusting the positions and/or angles of the light irradiators 130.

According to the embodiment of the present invention, the first actuators 150 of the actuators serve to tilt the base parts 120 to given angles or move the base parts 120 forward or backward toward or from the user's body. According to the embodiment of the present invention, each first actuator 150 includes a linear motor.

According to the present invention, the second actuators 160 of the actuators are provided correspondingly to the respective light irradiators 130 to move the light irradiators 130 forward or backward toward or from the user's body. According to the embodiment of the present invention, each second actuator 160 includes a linear motor.

An explanation of the operations of the first actuators 150 and the second actuators 160 will be given in detail with reference to FIG. 3.

Figure 3:
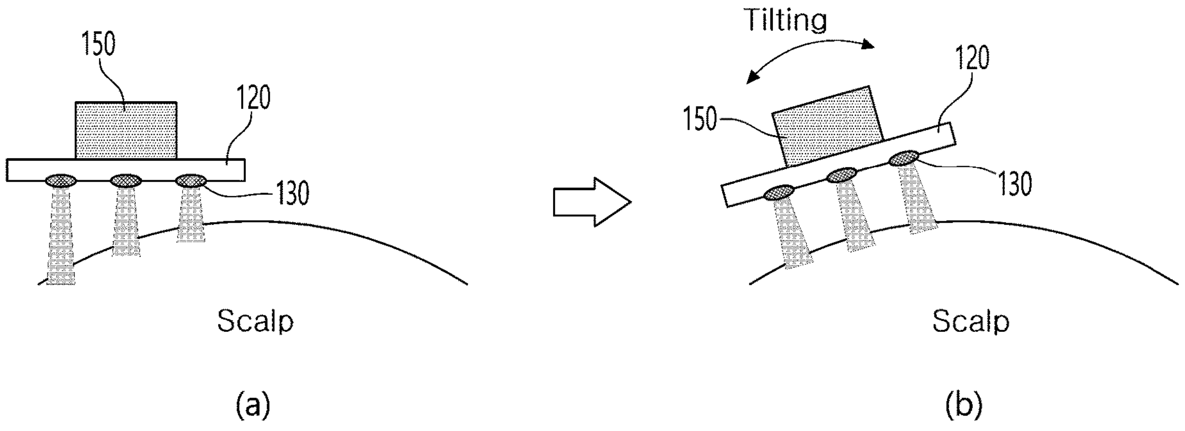
FIG. 3 shows a method for tilting the base part by means of a first actuator.

FIG. 3 shows a method for tilting the base part by means of the first actuator. FIG. 3(*a*) shows the angle and position of the base part 120 being at an initial state, and FIG. 3(*b*) shows the angle and position of the base part 120 tilting to an appropriate angle toward the user's body.

As shown in FIG. 3(*a*), the base part 120 does not face the surface of the user's body (the scalp in the embodiment of the present invention) accurately and is thus oriented toward the surface of the user's body at a somewhat misaligned angle therewith. In this case, the light emitted from the light irradiators 130 may be irradiated at somewhat misaligned angles, and accordingly, the light may not arrive at accurate positions of the scalp, so that the light is not transmitted well to the scalp to thus cause a large energy loss.

In this case, the first actuator 150 serves to tilt the base part 120 to allow the base part 120 to be adjusted at angle and in position so that the light irradiators 130 can face the surface of the user's body (the scalp) accurately.

According to the embodiment of the present invention, the adjustment of the base part 120 at angle and in position is performed based on body scanning data. For example, the light irradiation apparatus 100 calculates a normal vector of the surface of the user's body based on the body scanning data, obtains a tilting angle at which the normal vector is parallel with a predetermined axis of the base part 120, and allows the first actuator 150 to adjust the base part 120 at angle and in position based on the tilting angle.

According to another embodiment of the present invention, meanwhile, the adjustment of the base part 120 at angle and in position may be performed according to predetermined irradiation modes. An explanation of the irradiation modes will be given in detail with reference to FIG. 4.

Figure 4:
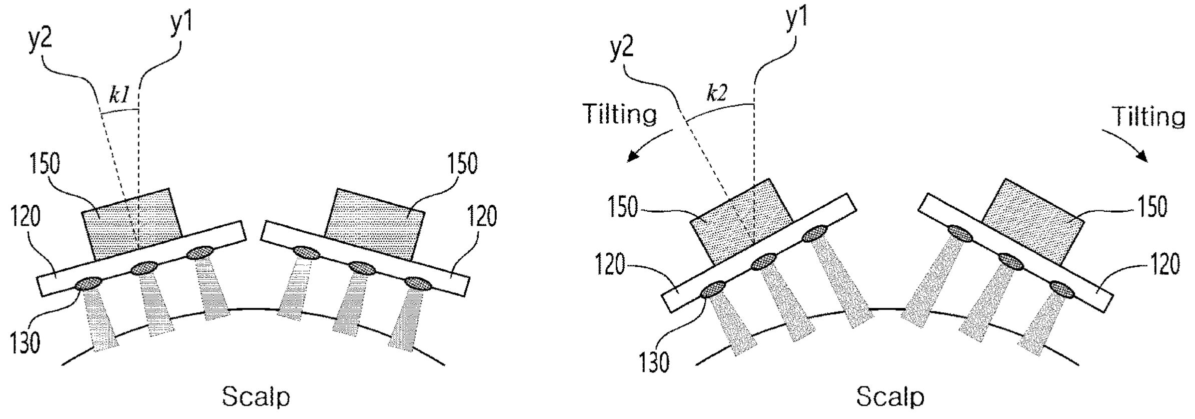
FIG. 4 shows the tilting operations of the base parts to the angles corresponding to irradiation modes according to the irradiation modes of the light irradiation apparatus according to the present invention.

FIG. 4 shows the tilting operations of the base parts to the angles corresponding to irradiation modes according to the irradiation modes of the light irradiation apparatus according to the present invention. FIG. 4(*a*) shows the positions and angles of the base parts 120 in a basic irradiation mode, and FIG. 4(*b*) shows the positions and angles of the base parts 120 in an irradiation mode for the top of the head.

Referring to FIG. 4(*a*), a state where light is irradiated on the scalp in the basic irradiation mode is shown. In the basic irradiation mode, the position and angle of the base part 120 are adjusted so that a predetermined axis y2 of the base part 120 is parallel with the normal vector of the scalp on which the light is irradiated.

Referring to FIG. 4(*b*), a state where light is irradiated on the scalp in the irradiation mode for the top of the head is shown. The irradiation mode for the top of the head is a mode set to concentratedly irradiate light on the top of the head. In the irradiation mode for the top of the head, the first actuator 150 tilts the left and right base parts 120 to the center of the scalp so that the light emitted from the light irradiators 130 are concentratedly irradiated on the top of the head, that is, the center of the scalp.

According to the embodiment of the present invention, the first actuator 150 tilts the base part 120 to an angle corresponding to each irradiation mode. For example, an angle between the predetermined axis y2 of the base part 120 and a vertical axis y1 of a global coordinate system is k1 in the basic irradiation mode and k2 in the irradiation mode for the top of the head, which are predetermined. In this case, if the angle is not k1 in the basis irradiation mode, the first actuator 150 tilts the base part 120 to make the angle become k1. If the angle is not k2 in the irradiation mode for the top of the head, the first actuator 150 tilts the base part 120 to make the angle become k2.

In the embodiment of the present invention as shown in FIG. 4, the tilt of the base part 120 has been explained in the irradiation mode for the top of the head, but the base part 120 may tilt to angles according to various irradiation modes, such as an irradiation mode for the front of the head, an irradiation mode for the back of the head, an irradiation mode for the sides of the head, and the like. In this case, the tilting angles of the base part 120 are adjusted so that light is concentratedly irradiated on the front of the head in the irradiation mode for the front of the head, on the back of the head in the irradiation mode for the back of the head, and on the sides of the head in the irradiation mode for the sides of the head.

Figure 5:
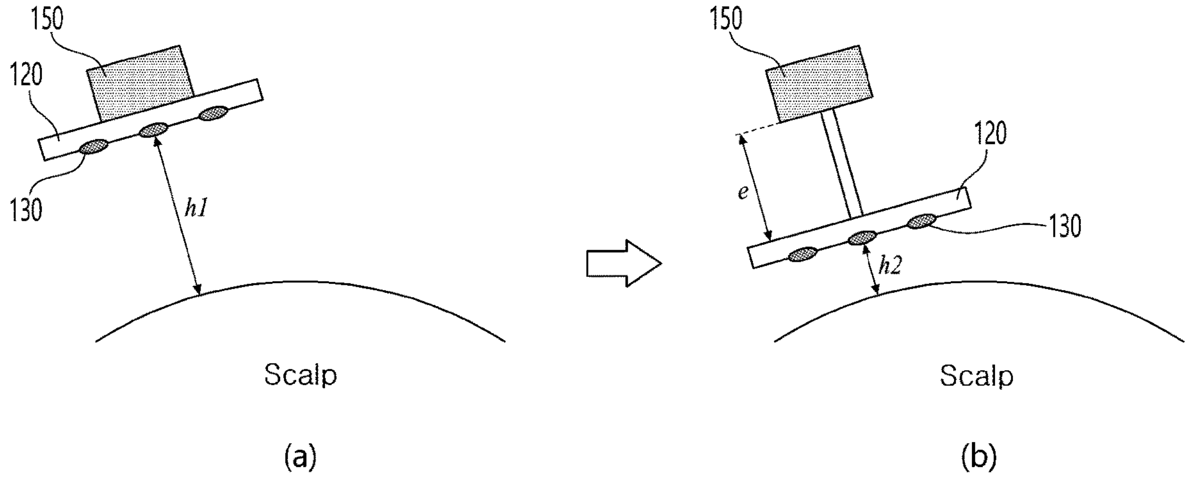
FIG. 5 shows a method for adjusting a distance between the base part and a user's body by means of the operation of the first actuator.

FIG. 5 shows a method for adjusting a distance between the base part and the user's body by means of the operation of the first actuator.

If the base part 120 has a long distance from the user's body, it is hard that the light emitted from the light irradiators 130 completely arrive at the surface of the user's body, thereby causing an energy loss. Contrarily, if the base part 120 is close to the user's body, the intensity of the light coming into contact with the surface of the user's body may become too strong.

So as to solve such problems, the first actuator 150 moves the base part 120 toward or from the user's body and thus adjusts the distance therebetween so that the base part 120 has an optimal distance from the user's body.

Referring to FIG. 5, a distance h1 between the base part 120 and the user's body (the scalp) in FIG. 5(*a*) is adjusted to a distance h2 as the base part 120 moves toward the scalp by a distance e by means of the operation of the first actuator 150.

Figure 6:
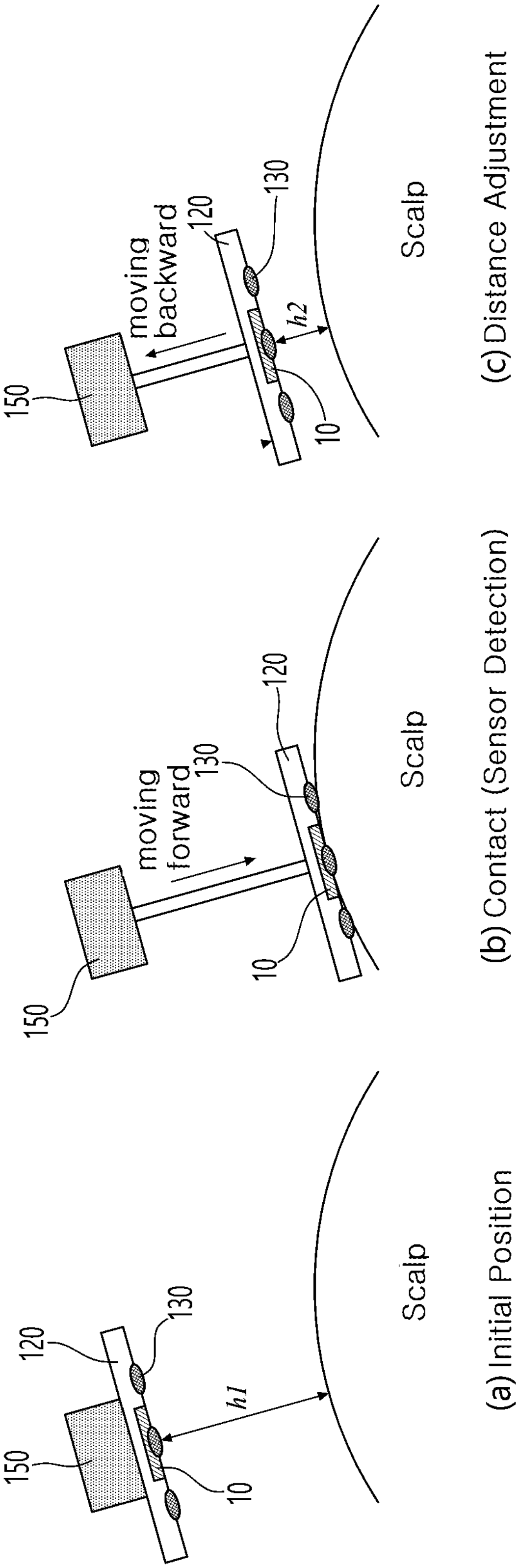
FIG. 6 shows a method for moving the base part from the user's body by an optimal distance according to the operation of a sensor.

FIG. 6 shows a method for moving the base part from the user's body by an optimal distance according to the operation of a sensor. If it is assumed that an optimal distance between the base part 120 and the user's body is h2, it is necessary that the position of the user's body is detected accurately and the position of the base part 120 distant by the distance h2 from the user's body is calculated accurately so as to allow the distance between the base part 120 and the user's body to be adjusted to the distance h2. According to the embodiment of the present invention, the necessaries are satisfied using a contact sensor. Hereinafter, the method for moving the base part 120 from the user's body by the optimal distance h2 according to the operation of the contact sensor will be explained with reference to FIG. 6.

FIG. 6(*a*) shows a state where the base part 120 is distant by an initial distance h1 from the user's body (the scalp in the embodiment of the present invention). In this case, the base part 120 includes the contact sensor 10 for detecting a contact between the base part 120 and the user's body. According to the embodiment of the present invention, the contact sensor 10 may be a pressure sensor.

FIG. 6(*b*) shows a state where the base part 120 moves forward toward the user's body by means of the operation of the first actuator 150 and thus comes into contact with the user's body. In this case, the contact sensor 10 detects a contact pressure between the base part 120 and the user's body, and if the detected contact pressure is over a threshold value, the detected signal is transmitted to the light irradiation apparatus 100. If the light irradiation apparatus 100 receives the detected signal from the contact sensor 10, it is determined that the base part 120 is brought into close contact with the user's body.

FIG. 6(*c*) shows a state where after the determination, the first actuator 150 operates in response to the determination to move the base part 120 backward from the user's body so that the base part 120 has the optimal distance h2 from the user's body. If the base part 120 has the optimal distance h2 from the user's body, the light irradiators 130 start to emit light so that the light is irradiated on the user's body.

According to the embodiment of the present invention, the method for adjusting the distance between one base part 120 and the user's body has been suggested, but the same method as in the above is carried out for the plurality of base parts 120, independently of one another. For example, if N base parts 120 are provided for the light irradiation apparatus 100, they can be adjusted in position and spaced apart from the user's body by optimal distances by means of the respective first actuators 150.

Under the method for adjusting the distances between the base parts 120 and the user's body, the base parts 120 are automatically adjusted in position in accordance with the shapes or sizes of the user's body, so that even though the user's body is hidden by hair or the light is not transmitted well owing to the irregular shape of the user's body, the light can be transmitted effectively to the user's body.

Further, because the distances between the base parts 120 and the user's body are automatically adjusted to the optimal distances, the light loss occurring until the irradiated light reaches the user's body can be minimized, and the light with optimal intensity can be irradiated on the user's body.

According to the embodiment of the present invention, further, the base part 120 approaches the user's body over a given distance or time, but if it is detected that the base part 120 does not touch the user's body, it is determined that the user's body does not exist on a position on which the light is irradiated, so that the power of the light irradiation apparatus 100 is turned off. An explanation of a method for controlling the power of the light irradiation apparatus 100 will be given in detail with reference to FIG. 7.

Figure 7:
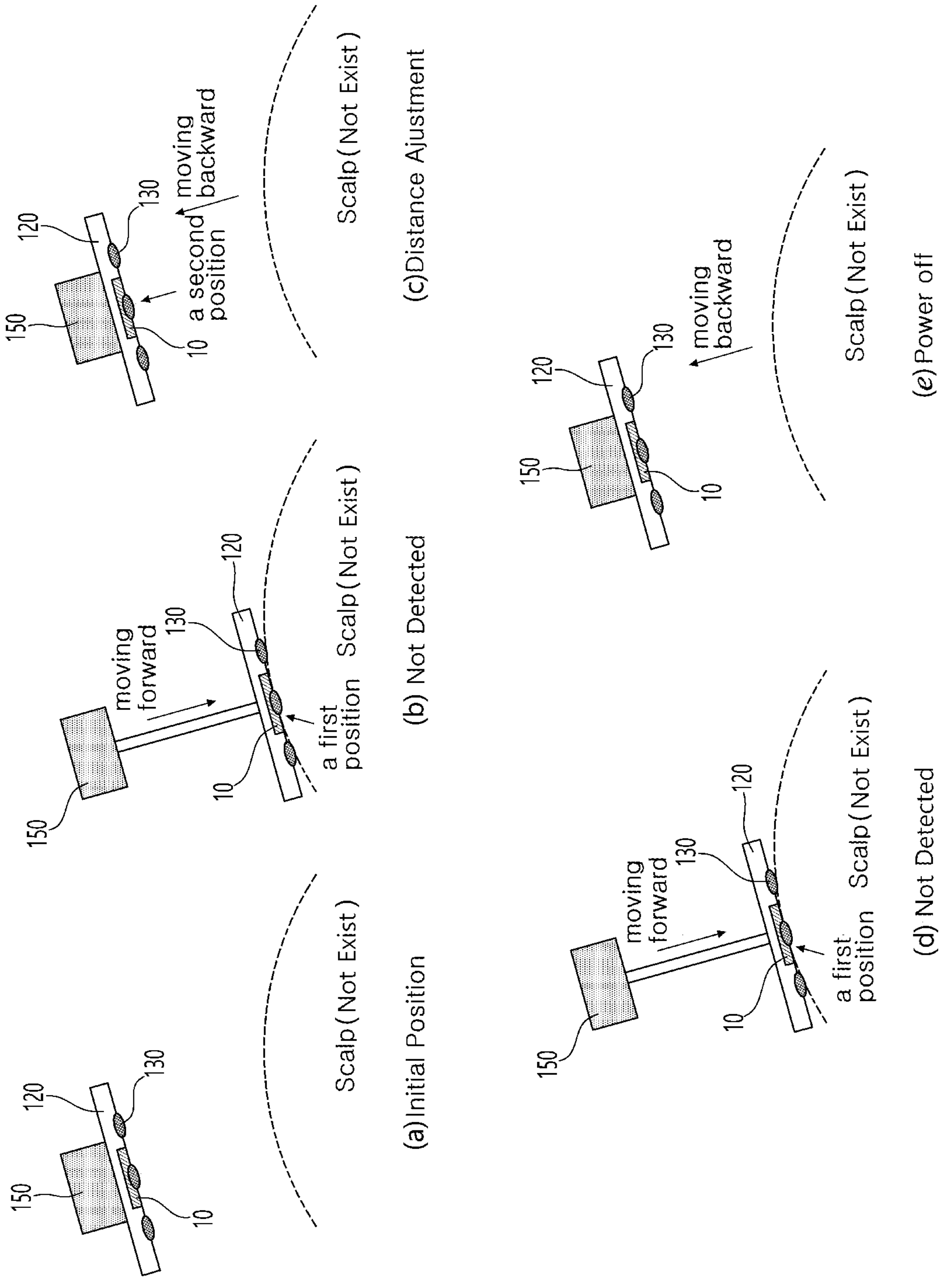
FIG. 7 shows a method for controlling the power of the light irradiation apparatus 100 according to the detection of the contact between the base part and the user's body.

FIG. 7 shows a method for controlling the power of the light irradiation apparatus 100 according to the detection of the contact between the base part and the user's body.

In FIG. 7(*a*), the base part 120 is at an initial position. According to the embodiment of the present invention, however, it is assumed that the user's body (that is, the scalp) does not exist on a position where the user's body has to be located.

In FIG. 7(*b*), the base part 120 moves forward toward a first position by means of the operation of the first actuator 150. In this case, the first position is a predetermined position where the user's body is expected to exist, and the first position is a position of the base part 120 moving from the initial position thereof by a predetermined distance or for a predetermined time in an operating direction of the first actuator 150.

According to the embodiment of the present invention, however, because it is assumed that the user's body (that is, the scalp) does not exist on a position where the user's body has to be located, even if the base part 120 moves to the first position, no contact between the base part 120 and the user's body is detected by means of the contact sensor 10.

In FIG. 7(*c*), if no contact between the base part 120 and the user's body is detected, the base part 120 moves backward toward a second position. In this case, the second position is the initial position as shown in FIG. 7(*a*) or an arbitrary position between the initial position and the first position.

In FIG. 7(*d*), the base part 120 moves forward toward the first position by means of the operation of the first actuator 150 after moving to the second position.

Even though the user's body does not exist on the corresponding position after the base part 120 has moved back to the first position, no contact between the base part 120 and the user's body is still detected by means of the contact sensor 10.

In FIG. 7(*e*), if it is detected again that no contact between the base part 120 and the user's body occurs, the base part 120 moves to the initial position, and the light irradiation apparatus 100 determines that the user's body does not exist on the position where the light is irradiated to thus turn off the power thereof.

If the user's body does not exist on the position where the light is irradiated, according to the embodiment of the present invention as shown in FIG. 7, the light irradiation apparatus 100 automatically detects the non-existence of the user's body and turns off the power, thereby efficiently performing power control.

According to the embodiment of the present invention as shown in FIG. 7, further, the reason why the detection of the contact between the base part 120 and the user's body is checked over at least two times is that the light irradiation apparatus 100 may be temporarily taken off or escape from the user's body, and accordingly, it is checked at least two times whether the user's body exists on the position where the light is irradiated.

Figure 8:
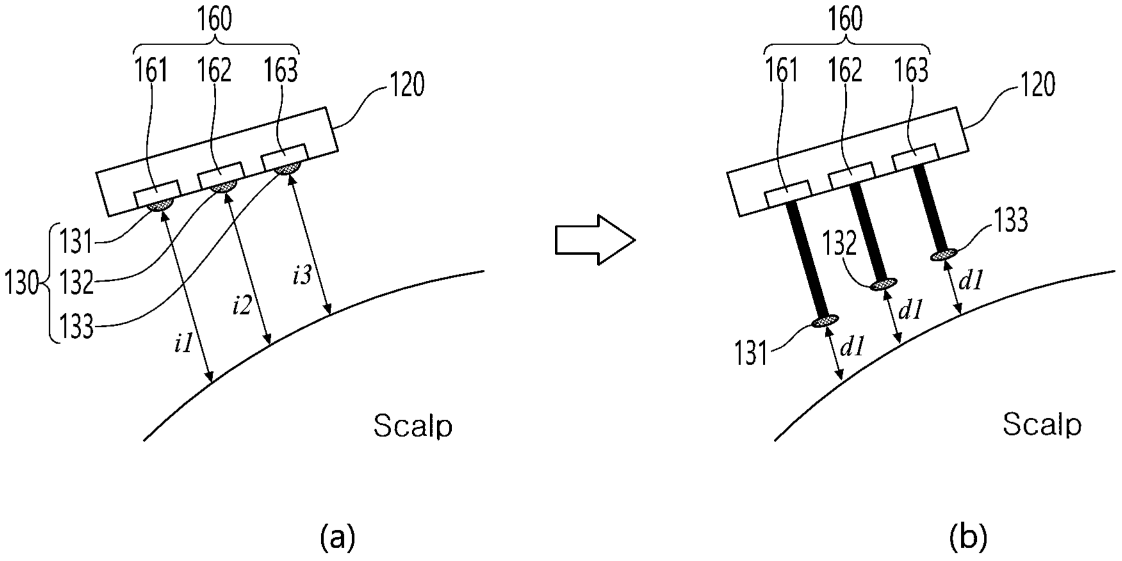
FIG. 8 shows a method for adjusting distances between the light irradiators and the surface of the user's body by means of second actuators.

FIG. 8 shows a method for adjusting distances between the light irradiators and the surface of the user's body by means of second actuators.

If the light irradiators 130 have long distances from the user's body, it is hard that the light irradiated from the light irradiators 130 fully reaches the surface of the user's body, and an energy loss occurs. Contrarily, if the light irradiators 130 have short distances from the user's body, the intensity of the light contacting with the surface of the user's body is excessively strong.

Further, if the plurality of light irradiators having a first light irradiator 131, a second light irradiator 132, and a third light irradiator 133 are disposed on one base part 120, distances between the first to third light irradiators 131 to 133 and the user's body may be different because of a difference between the surface curvature of the base part 120 and the surface curvature of the user's body (the scalp). In this case, the light reaching the user's body may be irradiated with different intensity according to the positions on which the light is irradiated, thereby undesirably causing the irradiation of the light with irregular intensity.

To solve such a problem, the second actuators 160 move the light irradiators 130 forward or backward toward or from the user's body and adjust the distances between the light irradiators 130 and the user's body, so that the light irradiators 130 can be distant from the user's body by optimal distances.

In FIG. 8(*a*), distances between the first to third light irradiators 131 to 133 and the user's body (the scalp) are i1, i2, and i3, but in FIG. 8(*b*), the distances between the first to third light irradiators 131 to 133 and the user's body (the scalp) are adjusted to the same distance d1 by means of the operations of the second actuators 160.

Figure 9:
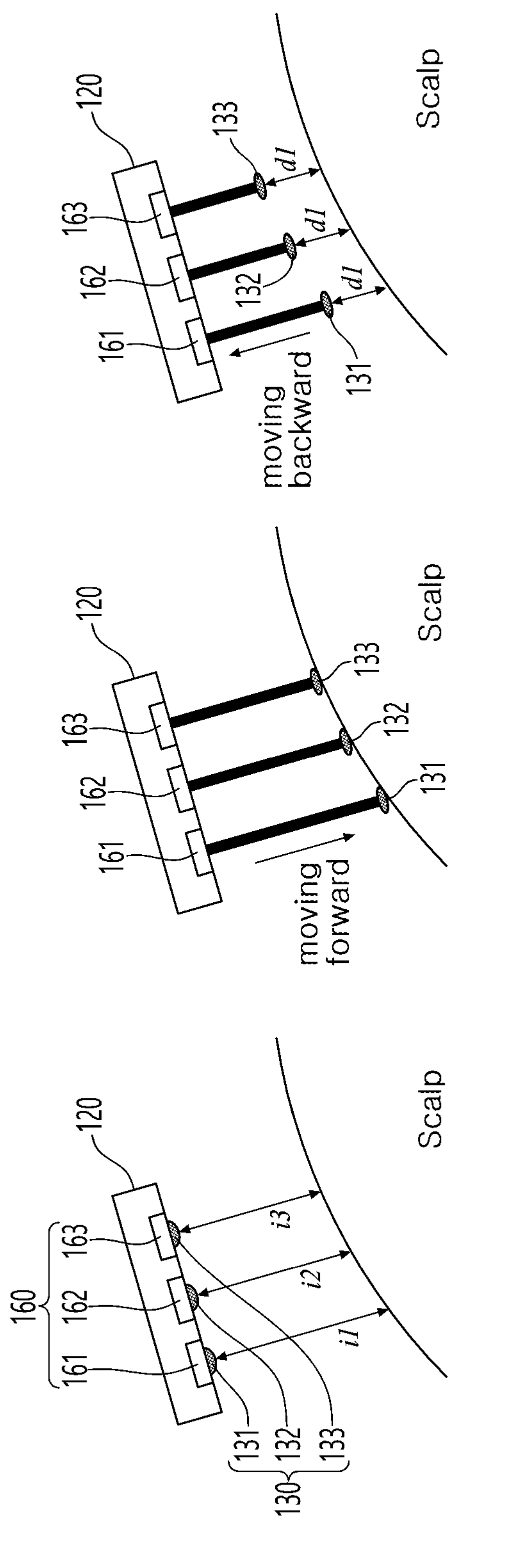
FIG. 9 shows an exemplary method for allowing the light irradiators to be spaced apart from the surface of the user's body by optimal distances under the detection of the sensors.

FIG. 9 shows an exemplary method for allowing the light irradiators to be spaced apart from the surface of the user's body by optimal distances under the detection of the sensors.

In the same manner as in the adjustment of the distance between the base part 120 and the user's body as shown in FIG. 6, if it is assumed that optimal distances between the light irradiators 130 and the user's body are d1, it is necessary that the position of the user's body is accurately detected and the position spaced apart from the user's body by the distance d1 is accurately calculated so as to adjust the distances between the light irradiators 130 and the user's body to the optimal distances d1. According to the embodiment of the present invention, such necessities are satisfied by using contact sensors. Hereinafter, an explanation of the method for adjusting the distances between the light irradiators and the user's body using the contact sensors will be given with reference to the attached drawings.

FIG. 9(*a*) shows a state where the light irradiators 131, 132, and 133 disposed on the base part 120 are distant from the user's body (the scalp) by different distances i1, i2 and i3. In this case, the second actuators 161, 162, and 163 corresponding to the light irradiators 131, 132, and 133 are disposed on the base part 120. The second actuators 161, 162, and 163 serve to adjust the light irradiators 131, 132, and 133 corresponding thereto in position. According to the embodiment of the present invention, the second actuators 161, 162, and 163 include linear motors.

Further, the base part 120 includes the contact sensors (not shown) for detecting contacts between the light irradiators 131, 132, and 133 and the user's body. According to the embodiment of the present invention, the contact sensors may pressure sensors. According to the embodiment of the present invention, the contact sensors may be built in the respective light irradiators 131, 132, and 133 or in the respective second actuators 161, 162, and 163.

FIG. 9(*b*) shows a state where the light irradiators 131, 132, and 133 move forward toward the user's body by means of the operations of the second actuators 161, 162, and 163 and thus come into contact with the user's body. In this case, the contact pressures between the light irradiators 131, 132, and 133 and the user's body are detected by the contact sensors, and if the detected contact pressures are over a threshold value, the detected signals are transmitted to the light irradiation apparatus 100. If the light irradiation apparatus 100 receives the detected signals from the contact sensors, it determines that the light irradiators 131, 132, and 133 corresponding to the detected signals come into contact with the user's body.

FIG. 9(*c*) shows a state where, in response to the determination of the light irradiation apparatus 100, the light irradiators 131, 132, and 133 move backward from the user's body by means of the operations of the second actuators 161, 162, and 163 so that they are spaced apart from the user's body by the optimal distances d1. If the light irradiators 131, 132, and 133 are spaced apart from the user's body by the optimal distances d1, light emitted from the light irradiators 131, 132, and 133 is irradiated on the user's body.

Under the method for adjusting the distances between the light irradiators 131, 132, and 133 and the user's body, the light irradiators 131, 132, and 133 are automatically adjusted in position in accordance with the shapes or sizes of the user's body, so that even though the user's body us hidden by hair or light is not transmitted well owing to the irregular shape of the user's body, the light can be transmitted effectively to the user's body.

Further, because the distances between the light irradiators 131, 132, and 133 and the user's body are automatically adjusted to the optimal distances, the light loss occurring until the irradiated light reaches the user's body can be minimized, and the light with optimal intensity can be irradiated on the user's body, thereby preventing the light with irregular intensity from being irradiated.

Figure 10:
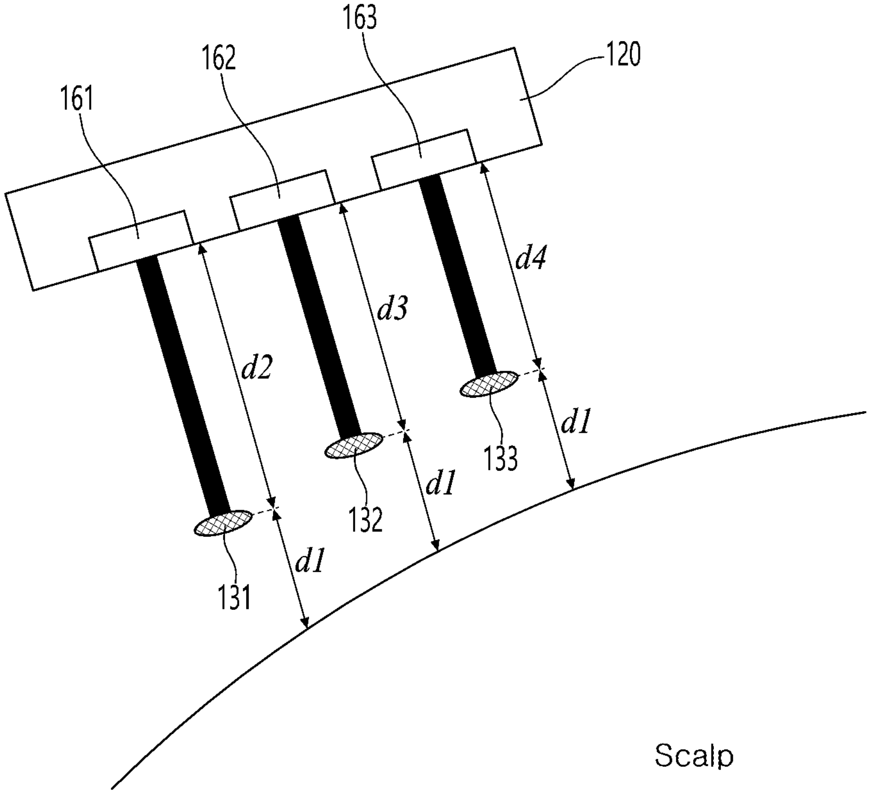
FIG. 10 shows a state where the light irradiators are spaced apart from the user's body by the optimal distances.

FIG. 10 shows a state where the light irradiators are spaced apart from the user's body by the optimal distances. According to the present invention, FIG. 10 shows a state where the distances between the light irradiators 131, 132, and 133 and the user's body are adjusted to the distances d1 by means of the operations of the second actuators 161, 162, and 163 as shown in FIG. 8.

Referring to FIG. 10, because of a difference between the surface curvature of the base part 120 and the surface curvature of the user's body, if the distances between the light irradiators 131, 132, and 133 and the user's body are adjusted to the same optimal distance d1 as one another, it can be appreciated that the extending distances of the light irradiators 131, 132, and 133 from the base part 120 are different from one another as distances d2, d3, and d4.

According to the present invention, the intensity of light irradiated on the user's body from the light irradiators 131, 132, and 133 becomes different based on the user's body scanning data.

For example, if the user's body scanning data is analyzed to recognize the features of the user's body, the intensity of light irradiated on the user's body around the features may be adjusted. For example, it is assumed that default intensity of light irradiated from the light irradiators 131, 132, and 133 is 1. In this case, if a scar exists at a position on which the light emitted from the first irradiator 131 is irradiated, the intensity of light irradiated from the first irradiator 131 is lowered to zero, and the intensity of light irradiated from the second irradiator 132 adjacent to the first irradiator 131 is lowered to 0.5, so as to prevent the scar from being serious by means of the light. The intensity of light irradiated from the third irradiator 133 somewhat distant from the first irradiator 131 is kept to 1. Otherwise, if thick dandruff exists at a position on which the light emitted from the first irradiator 131 is irradiated, the intensity of light irradiated from the first irradiator 131 is raised to 2, and the intensity of light irradiated from the second irradiator 132 adjacent to the first irradiator 131 is raised to 1.5, so as to allow light energy capable of passing through the thick dandruff to be sufficiently irradiated. The intensity of light irradiated from the third irradiator 133 somewhat distant from the first irradiator 131 is kept to 1.

According to the embodiment of the present invention, further, the light irradiators 131, 132, and 133 approach the user's body over a given distance or time, but if it is detected that the light irradiators 131, 132, and 133 do not come into contact with the user's body, it is determined that the user's body does not exist on a position on which light is irradiated, so that the power of the light irradiation apparatus 100 is turned off. An explanation of a method for controlling the power of the light irradiation apparatus 100 will be given in detail with reference to FIG. 11.

Figure 11:
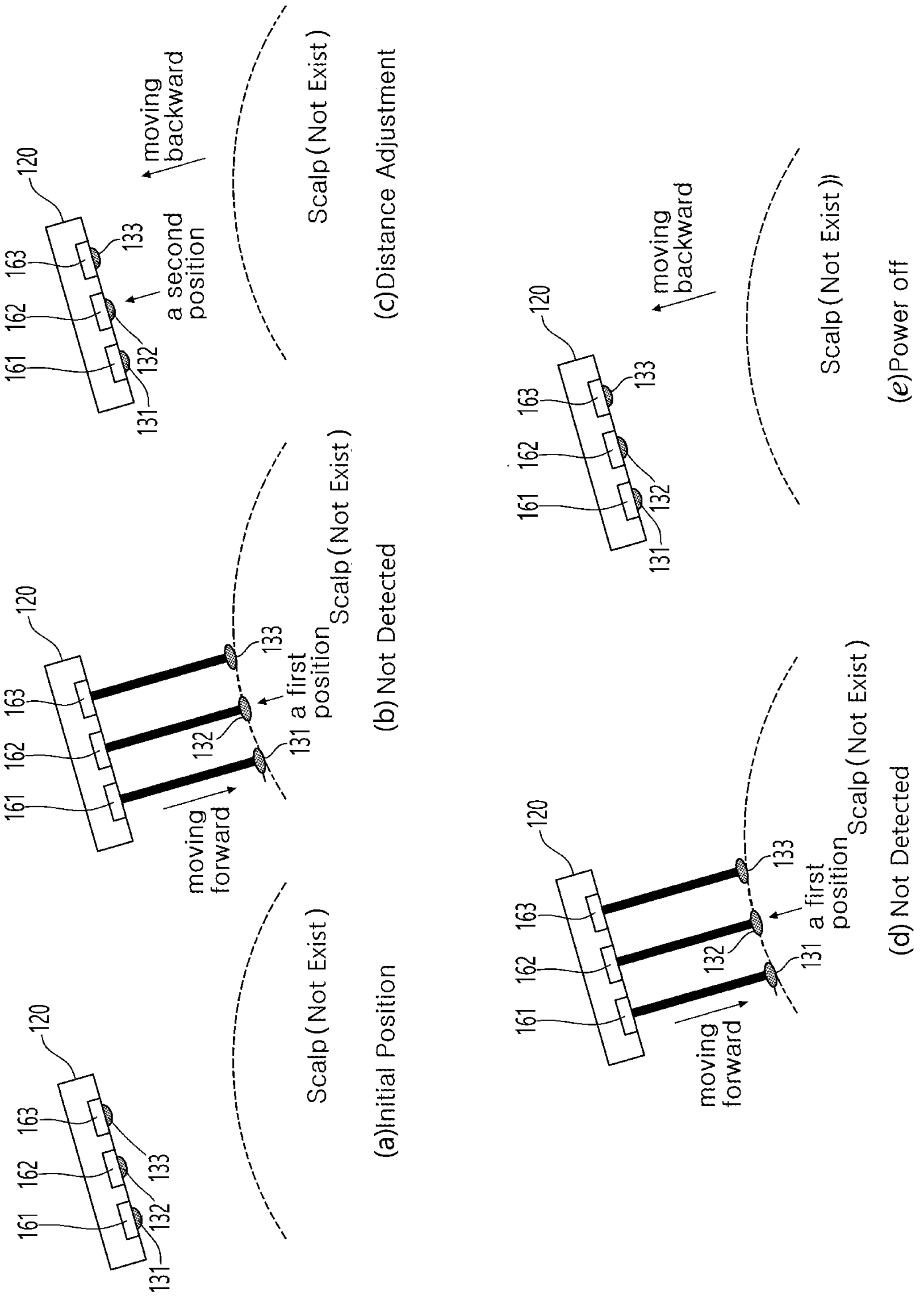
FIG. 11 shows a method for controlling the power of the light irradiation apparatus according to the detection of the contacts between the light irradiators and the user's body.

FIG. 11 shows a method for controlling the power of the light irradiation apparatus 100 according to the detection of the contacts between the light irradiators and the user's body.

In FIG. 11(*a*), the light irradiators 131, 132, and 133 are at initial positions. According to the embodiment of the present invention, however, it is assumed that the user's body (that is, the scalp) does not exist on a position where the user's body has to be located.

In FIG. 11(*b*), the light irradiators 131, 132, and 133 move forward toward first positions by means of the operations of the second actuators 161, 162, and 163. In this case, the first positions are predetermined positions where the user's body is expected to exist, and the first positions are positions of the light irradiators 131, 132, and 133 moving from the initial positions thereof by predetermined distances or for a predetermined time in operating directions of the second actuators 161, 162, and 163.

According to the embodiment of the present invention, however, because it is assumed that the user's body (that is, the scalp) does not exist on a position where the user's body has to be located, even if the light irradiators 131, 132, and 133 move to the first positions, no contacts between the light irradiators 131, 132, and 133 and the user's body are detected by means of the contact sensors (not shown).

In FIG. 11(*c*), if no contacts between the light irradiators 131, 132, and 133 and the user's body are detected, the light irradiators 131, 132, and 133 move backward toward second positions. In this case, the second positions are the initial positions as shown in FIG. 11(*a*) or arbitrary positions between the initial positions and the first positions.

In FIG. 11(*d*), the light irradiators 131, 132, and 133 move forward toward the first positions by means of the operations of the second actuators 161, 162, and 163 after moving to the second positions.

Even though the user's body does not exist on the corresponding position after the light irradiators 131, 132, and 133 have moved back to the first positions, no contacts between the light irradiators 131, 132, and 133 and the user's body are still detected by means of the contact sensor.

In FIG. 11(*e*), if it is detected again that no contacts between the light irradiators 131, 132, and 133 and the user's body occur, the light irradiators 131, 132, and 133 move to the initial positions, and the light irradiation apparatus 100 determines that the user's body does not exist on the position where light is irradiated to thus turn off the power.

If the user's body does not exist on the position where light is irradiated, according to the embodiment of the present invention as shown in FIG. 11, the light irradiation apparatus 100 automatically detects the non-existence of the user's body and thus turns off the power, thereby efficiently performing power control.

In the same manner as in FIG. 7, further, according to the embodiment of the present invention as shown in FIG. 11, the reason why the detection of the contacts between the light irradiators 131, 132, and 133 and the user's body is checked over at least two times is that the light irradiation apparatus 100 may be temporarily taken off or escape from the user's body, and accordingly, it is checked at least two times whether the user's body exists on the position where the light is irradiated.

Figure 12:
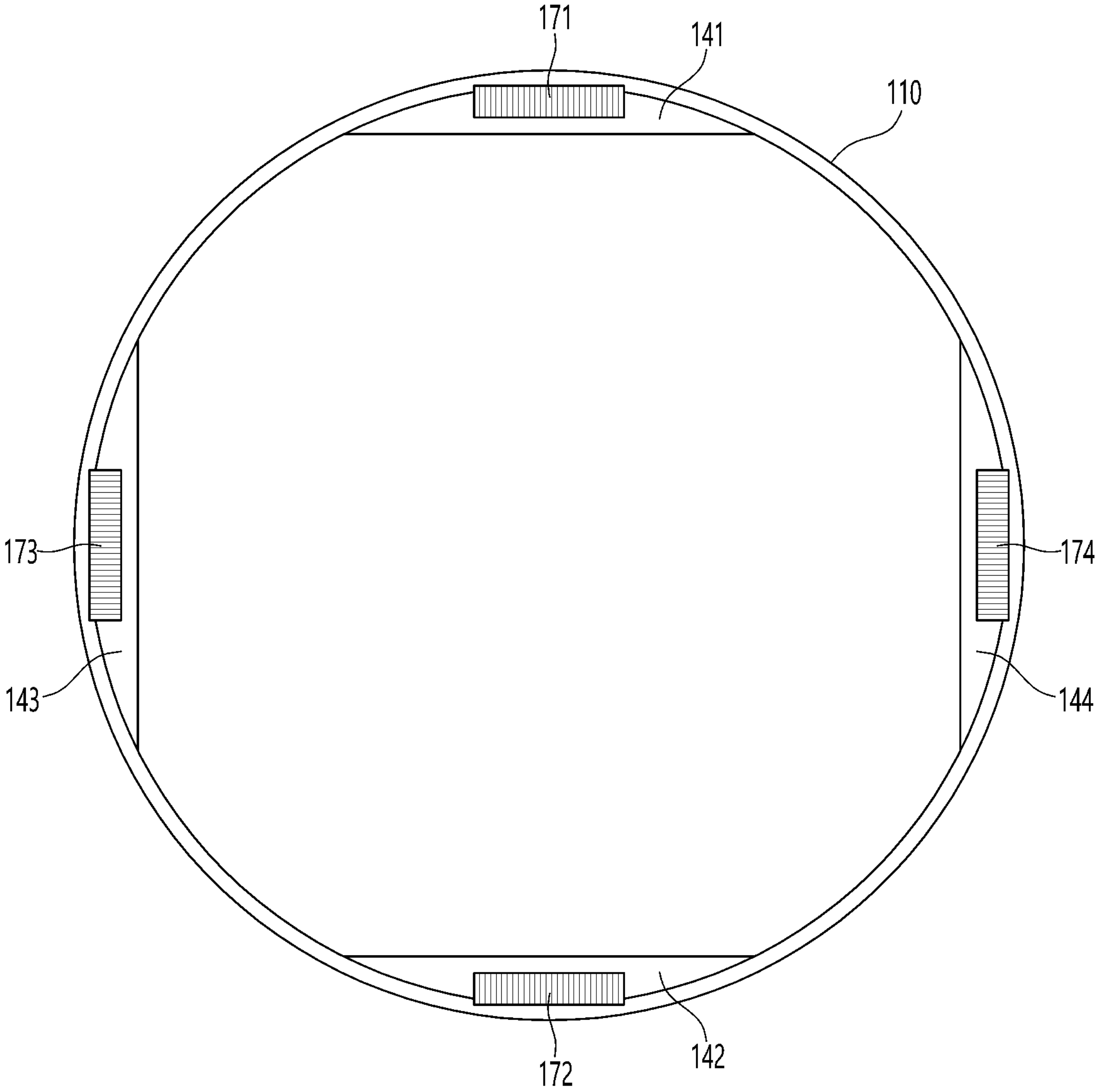
FIG. 12 shows an exemplary configuration of fixing parts according to the present invention.

FIG. 12 shows an exemplary configuration of the fixing parts. According to the embodiment of the present invention, the first fixing part 141 is disposed on the front of the interior of the light irradiation apparatus 100, the second fixing part 142 is on the back thereof, and the third and fourth fixing parts 143 and 144 on both sides thereof. However, they may be freely disposed inside the light irradiation apparatus 100, without being limited thereto. For example, the light irradiation apparatus 100 may have N different fixing parts arranged along the inner periphery of the body part 110.

A plurality of third actuators 171, 172, 173, and 174 corresponding to the first to fourth fixing parts 141, 142, 143, and 144 are disposed on the body part 110. The third actuators 171, 172, 173, and 174 move the corresponding first to fourth fixing parts 141, 142, 143, and 144 in the internal direction of the body part 110 to allow the first to fourth fixing parts 141, 142, 143, and 144 to come into close contact with the user's body. This process will be explained in detail with reference to FIG. 13.

Figure 13:
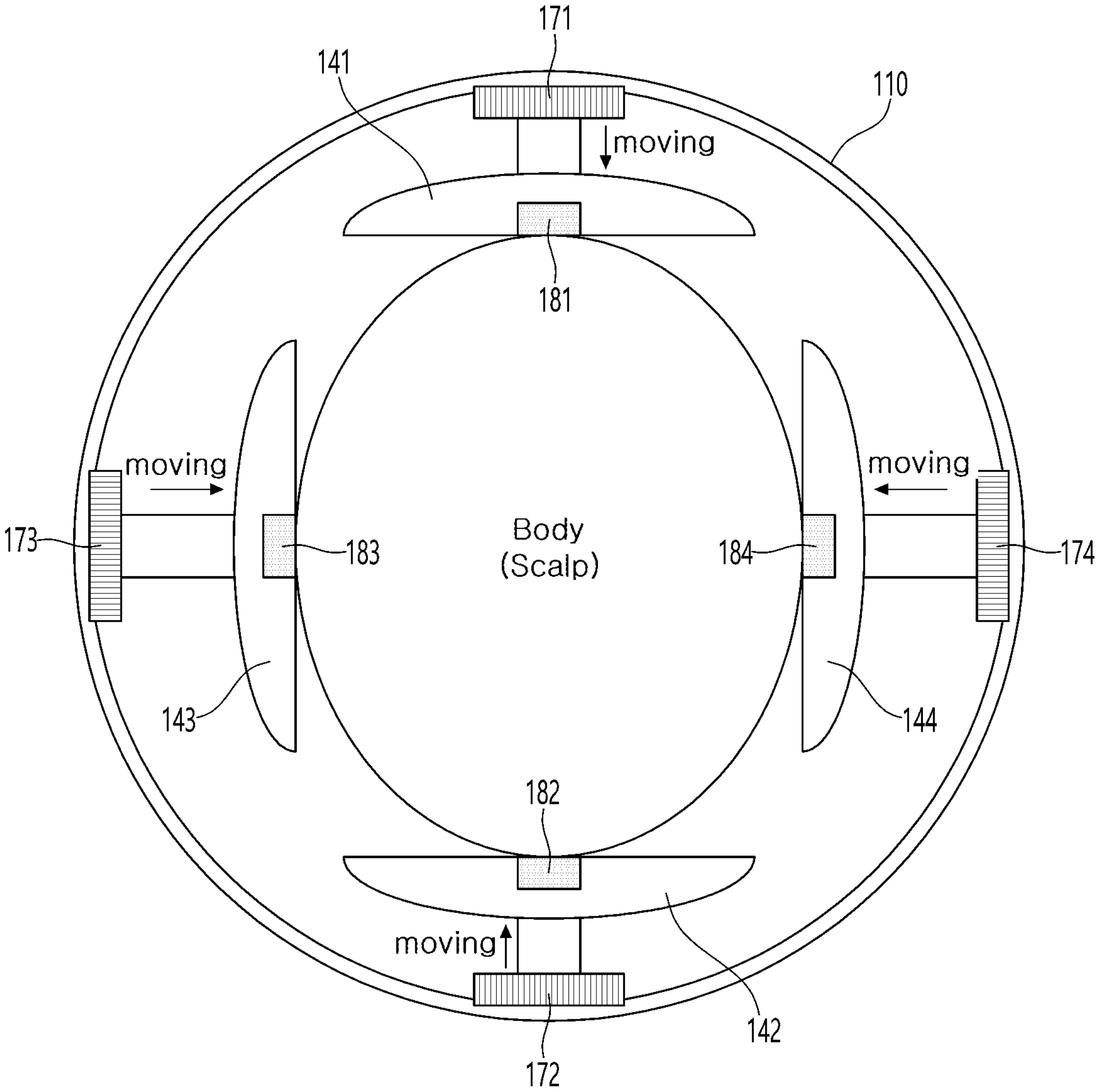
FIG. 13 shows a method for allowing the fixing parts to come into close contact with the surface of the user's body by means of the operations of third actuators.

FIG. 13 shows a method for allowing the fixing parts to come into close contact with the surface of the user's body by means of the operations of the third actuators.

If the user's body (the scalp in the embodiment of the present invention) is located inside the body part 110, the third actuators 171, 172, 173, and 174 operate to fix the body part 110 to the user's body. The third actuators 171, 172, 173, and 174 move the corresponding first to fourth fixing parts 141, 142, 143, and 144 in the internal direction of the body part 110 until the corresponding first to fourth fixing parts 141, 142, 143, and 144 come into close contact with the user's body. If the first to fourth fixing parts 141, 142, 143, and 144 come into close contact with the user's body, the third actuators 171, 172, 173, and 174 stop the movements of the first to fourth fixing parts 141, 142, 143, and 144, and in this state, the body part 110 is fixed to the user's body.

According to the embodiment of the present invention, the fixing parts 141, 142, 143, and 144 include contact sensors 181, 182, 183, and 184 corresponding thereto. The contact sensors 181, 182, 183, and 184 detect the contact pressures between the fixing parts 141, 142, 143, and 144 and the user's body, and if the detected contact pressures are over a threshold value, the detected signals are transmitted to the light irradiation apparatus 100. If the light irradiation apparatus 100 receives the detected signals from the contact sensors 181, 182, 183, and 184, it is determined that the fixing parts 141, 142, 143, and 144 are brought into close contact with the user's body, and the light irradiation apparatus 100 transmits control commands to the third actuators 171, 172, 173, and 174 so as to stop the movements of the fixing parts 141, 142, 143, and 144.

According to the embodiment of the present invention, the fixing parts 141, 142, 143, and 144 have cushions disposed on the surfaces coming into close contact with the user's body to release the compression occurring when the fixing parts 141, 142, 143, and 144 come into close contact with the user's body.

Figure 14:
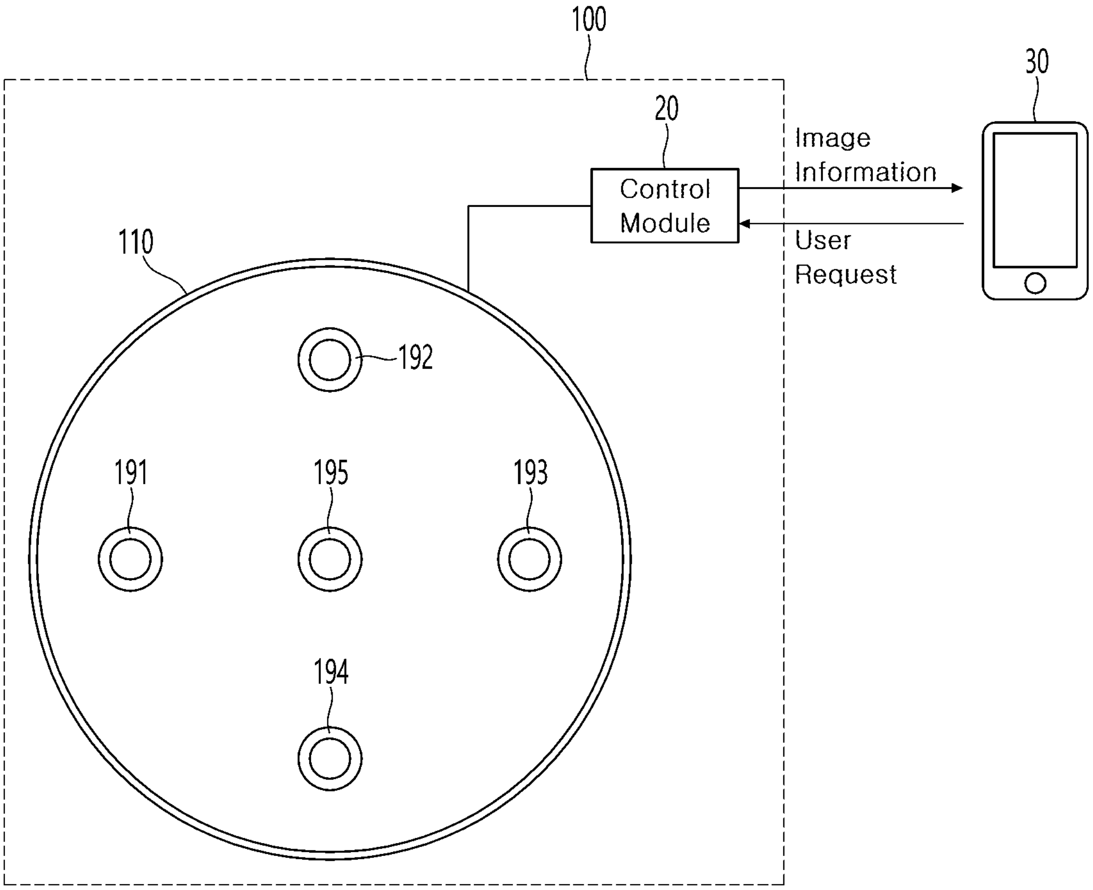
FIG. 14 shows a method for providing scalp image information for a user terminal by means of imaging parts.

FIG. 14 shows a method for providing scalp image information for a user terminal by means of imaging parts. According to the embodiment of the present invention, the light irradiation apparatus 100 may include one or more imaging parts 191, 192, 193, 194, and 195 and a control module 20 for controlling the imaging parts 191, 192, 193, 194, and 195.

According to the embodiment of the present invention, one or more imaging parts 191, 192, 193, 194, and 195 are distributedly located inside the body part 110.

According to the embodiment of the present invention, the control module 20 controls the general operations of the light irradiation apparatus 100 as well as the operations of the imaging parts 191, 192, 193, 194, and 195.

The imaging parts 191, 192, 193, 194, and 195 provide the images (e.g., the scalp images) for the user's body located inside the body part 110 for the control module 20. The control module 20 transmits the images as image information to a user terminal 30 through a communication interface (not shown). The user sees the images on the user terminal 30 to check his or her scalp state.

Further, the user transmits a user request to the control module 20 through the user terminal 30 so as to request additional information related to his or her the user's body. For example, if the user wants to know more specific scalp state of the top of the head after his or her scalp state has been checked through the user terminal 30, the user terminal 30 transmits the request of specific information of the top of the head as the user request to the control module 20. The control module 20 allows the imaging part 191 corresponding to the top of the head to take a picture for his or her top of the head with a higher resolution and then transmits the image as image information to the user terminal 30.

Figure 15:
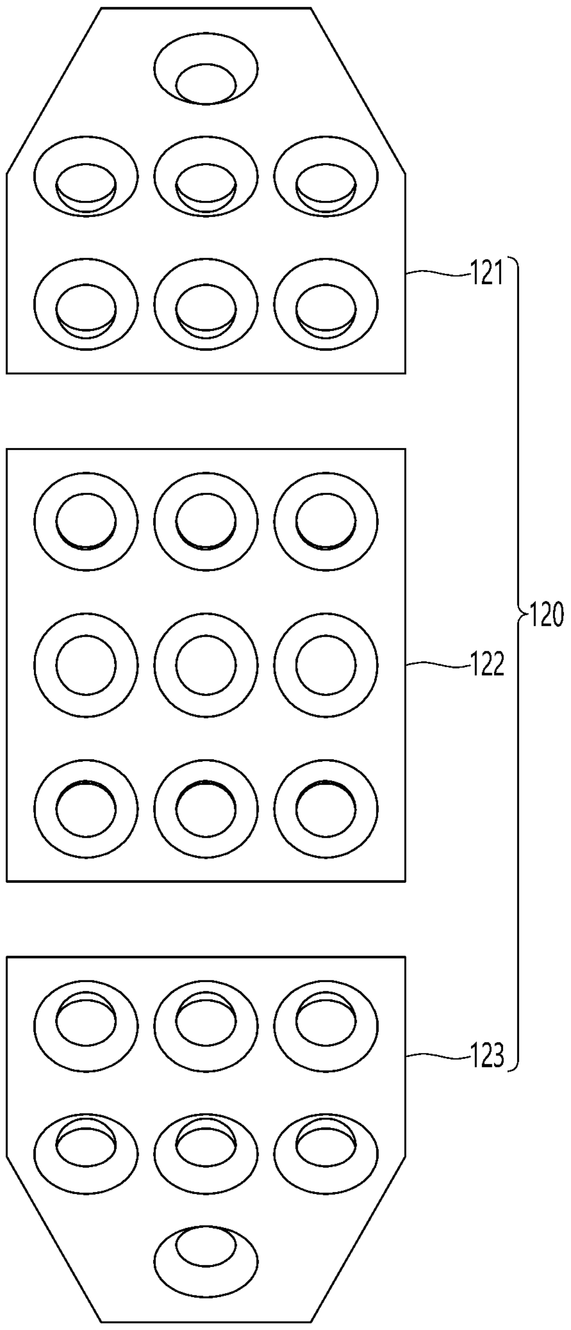
FIG. 15 shows another exemplary configuration of the base part according to the present invention.

FIG. 15 shows another exemplary configuration of the base part according to the present invention. In this case, one base part 120 is constituted of a plurality of sub-base parts 121, 122, and 123.

In FIG. 15, the base part 120 is constituted of three sub-base parts 121, 122, and 123 divided along a column thereof, but without being limited thereto, the base part 120 may be constituted of four or more sub-base parts divided along a row and a column thereof.

The sub-base parts 121, 122, and 123 are adjusted at angle and/or in position, independently of one another. To do this, the respective sub-base parts 121, 122, and 123 are provided with the corresponding first actuators (not shown). The operations and configurations of the first actuators are the same as of the first actuator 150 as explained with references, FIGS. 3 to 6, and therefore, explanations of the first actuators will be avoided.

Figure 16:
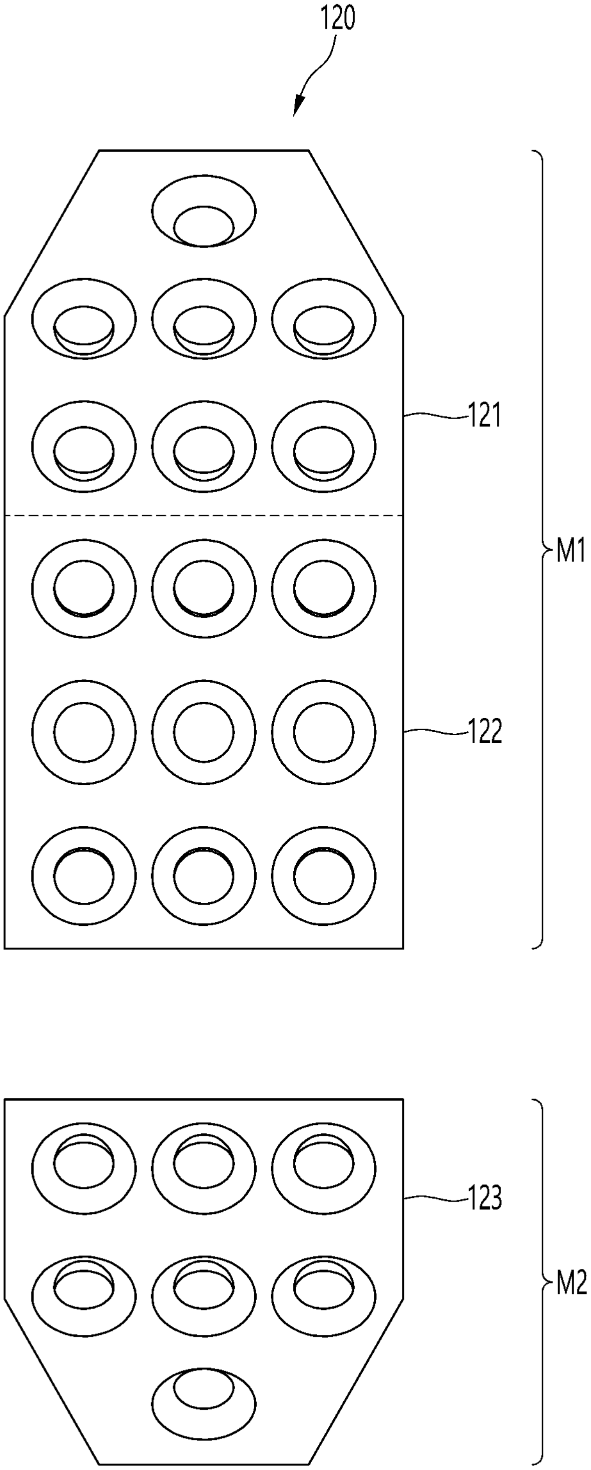
FIG. 16 shows an exemplary configuration of sub-base modules made by coupling the sub-base parts of FIG. 15 to each other.

FIG. 16 shows an exemplary configuration of sub-base modules made by coupling the sub-base parts of FIG. 15 to each other.

As described with reference to FIG. 15, the sub-base parts 121, 122, and 123 are adjusted at angle and/or in position, independently of one another, but some of them may be coupled or fastened to each other and thus operate as a single mechanical module.

For example, the first sub-base part 121 and the second sub-base part 122 of the sub-base parts 121, 122, and 123 are coupled or fastened to each other to constitute a first sub-module M1, and the remaining third sub-base part 133 constitutes a second sub-module M2. The first and second sub-modules M1 and M2 are adjusted at angle and/or in position, independently of each other.

In this case, the first sub-base part 121 and the second sub-base part 122 constituting the first sub-module M1 operate as the single integrated mechanical module and are thus adjusted at angle and/or in position in the state of being coupled or fastened to each other.

Figure 17:
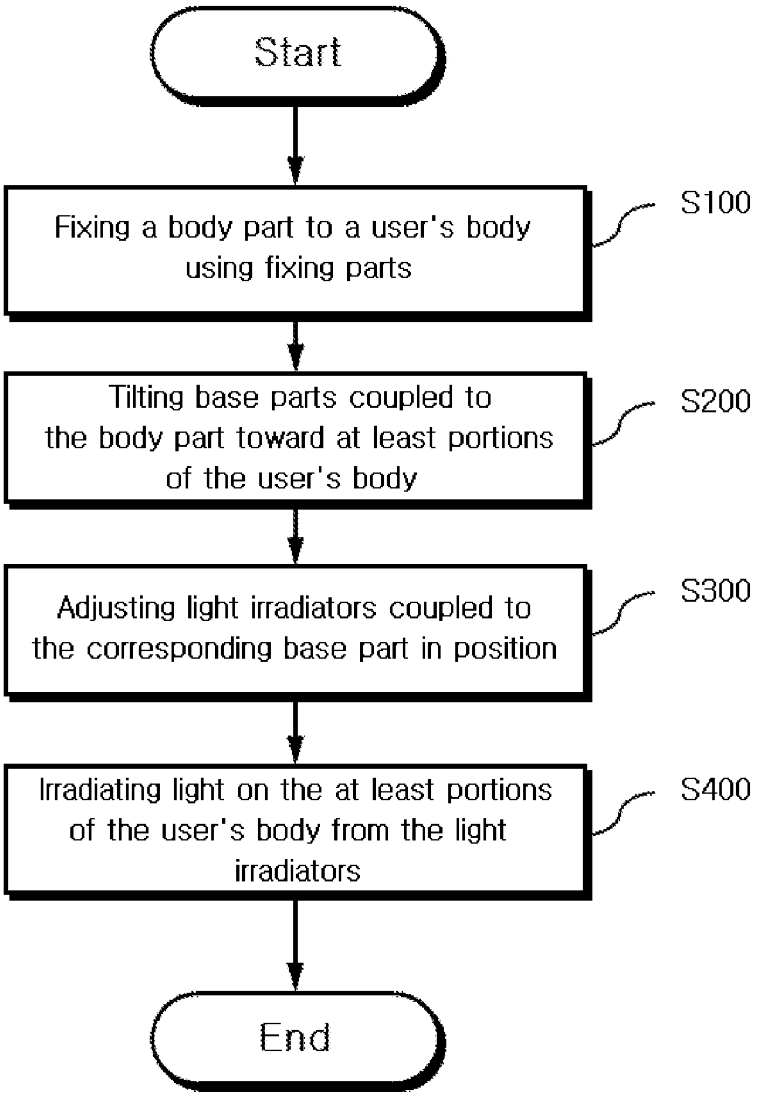
FIG. 17 is a flowchart showing a method for controlling a body-customized light irradiation apparatus according to the present invention.

FIG. 17 is a flowchart showing a method for controlling a body-customized light irradiation apparatus according to the present invention.

The light irradiation apparatus is the light irradiation apparatus 100 as described with references, FIGS. 1 to 14, and includes a body part, base parts coupled to the body part, light irradiators coupled to the corresponding base part to irradiate light on a user's body, fixing parts for fixing the body part to the user's body, and one or more actuators controlled by a computing device and serving as position adjustors for adjusting the light irradiators in position. The actuators may include first actuators for adjusting the base parts at angle and/or in position, second actuators for adjusting the light irradiators in position, and third actuators for allowing the fixing parts to come into close contact with the user's body.

The method for controlling the body-customized light irradiation apparatus according to the embodiment of the present invention is performed by automatically adjusting the light irradiators in position so that the light irradiators correspond to the user's body on which light is irradiated. In specific, the base parts are adjusted at angle and/or in position or the light irradiators are adjusted in position appropriately according to the shape or position of the user's body, so that the light irradiation angles or distances of the light irradiators can be adjusted appropriately according to the shape or position of the user's body.

Hereinafter, the method for controlling the body-customized light irradiation apparatus according to the present invention will be explained with reference to FIG. 17. According to the embodiment of the present invention, however, detailed explanations of the same contents as in FIGS. 1 to 16 will be avoided.

At step S100, the body part is fixed to the user's body. In this case, one or more fixing parts disposed on the body part move to the inside of the body part by means of the third actuators and come into close contact with the user's body, so that the body part is fixed to the user's body.

At step S200, the base parts tilt toward at least portions of the user's body. In this case, the base parts are adjusted at angles by means of the first actuators to allow the predetermined axes of the base parts to be parallel with the normal vector of the surface of the user's body, so that the base parts tilt.

At step S300, the light irradiators are adjusted in positions. In this case, the first actuators move the corresponding base parts forward and backward toward and from the user's body to allow the light irradiators to be spaced apart from the user's body by optimal distances, so that the light irradiators are adjusted in positions. Otherwise, the second actuators move the corresponding light irradiators forward and backward toward and from the user's body to allow the light irradiators to be spaced apart from the user's body by optimal distances, so that the light irradiators are adjusted in positions.

At step S400, light is irradiated on at least portions of the user's body from the light irradiators.

As described above, the body-customized light irradiation apparatus and the method for controlling the same according to the embodiments of the present invention can allow the light to be irradiated customizedly to the user's body to thus optimize the treatment effectiveness.

Further, the body-customized light irradiation apparatus and the method for controlling the same according to the embodiments of the present invention can allow the light to be irradiated on the user's body to be adjusted in position and at angle even though the user's body is curvedly or irregularly shaped.

Besides, the body-customized light irradiation apparatus and the method for controlling the same according to the embodiments of the present invention can allow the light to be irradiated on the user's body to be adjusted in distance to thus irradiate the light with optimal intensity on given positions of the user's body.

Hereinafter, an exemplary computing device 500 that can implement an apparatus and a system, according to various embodiments of the present invention, will be described with reference to FIG. 18. For example, the computing device 500 may be control module 20 depicted in FIG. 14.

Figure 18:
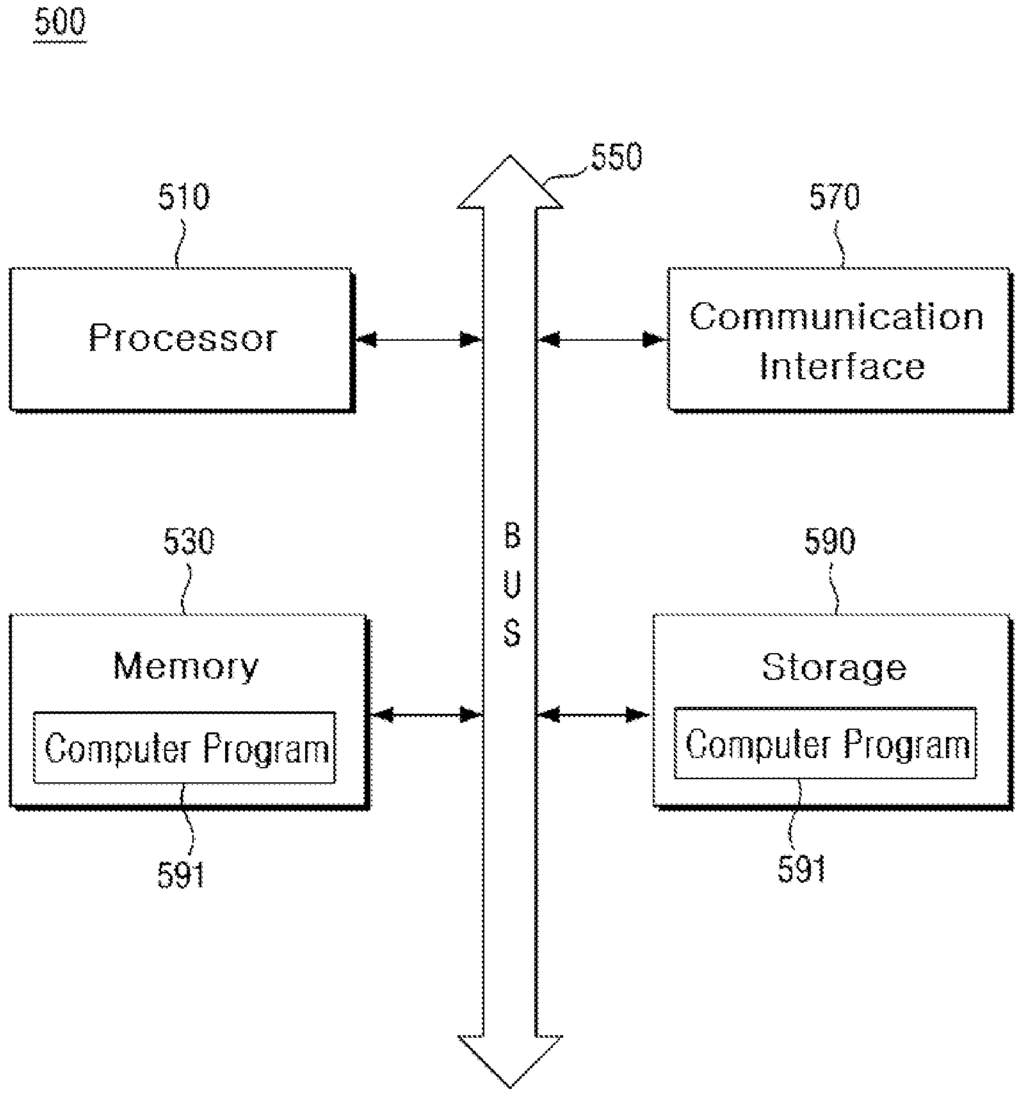
FIG. 18 is a block diagram showing an exemplary hardware configuration of a computing device for controlling operations according to present invention.

FIG. 18 is an example hardware diagram illustrating a computing device 500.

As shown in FIG. 18, the computing device 500 may include one or more processors 510, a bus 550, a communication interface 570, a memory 530, which loads a computer program 591 executed by the processors 510, and a storage 590 for storing the computer program 591. However, FIG. 18 illustrates only the components related to the embodiment of the present invention. Therefore, it will be appreciated by those skilled in the art that the present invention may further include other general purpose components in addition to the components shown in FIG. 18.

The processor 510 controls overall operations of each component of the computing device 500. The processor 510 may be configured to include at least one of a Central Processing Unit (CPU), a Micro Processor Unit (MPU), a Micro Controller Unit (MCU), a Graphics Processing Unit (GPU), or any type of processor well known in the art. Further, the processor 510 may perform calculations on at least one application or program for executing a method/operation according to various embodiments of the present invention. The computing device 500 may have one or more processors.

The memory 530 stores various data, instructions and/or information. The memory 530 may load one or more programs 591 from the storage 590 to execute methods/operations according to various embodiments of the present invention. An example of the memory 530 may be a RAM, but is not limited thereto.

The bus 550 provides communication between components of the computing device 500. The bus 550 may be implemented as various types of bus such as an address bus, a data bus and a control bus.

The communication interface 570 supports wired and wireless internet communication of the computing device 500. The communication interface 570 may support various communication methods other than internet communication. To this end, the communication interface 570 may be configured to comprise a communication module well known in the art of the present invention.

The storage 590 can non-temporarily store one or more computer programs 591. The storage 590 may be configured to comprise a non-volatile memory, such as a Read Only Memory (ROM), an Erasable Programmable ROM (EPROM), an Electrically Erasable Programmable ROM (EEPROM), a flash memory, a hard disk, a removable disk, or any type of computer readable recording medium well known in the art.

The computer program 591 may include one or more instructions, on which the methods/operations according to various embodiments of the present invention are implemented. For example, the computer program 591 comprises instructions for performing operations comprising fixing a body part to a user's body, tilting base parts coupled to the body part toward at least portions of the user's body, adjusting light irradiators coupled to the corresponding base part in position, and irradiating light on the at least portions of the user's body from the light irradiators, wherein the step of adjusting the light irradiators in position is performed so that the positions of the light irradiators correspond to the at least portions of the user's body on which the light is irradiated.

When the computer program 591 is loaded on the memory 530, the processor 510 may perform the methods/operations in accordance with various embodiments of the present invention by executing the one or more instructions.

The technical features of the present invention described so far may be embodied as computer readable codes on a computer readable medium. The computer readable medium may be, for example, a removable recording medium (CD, DVD, Blu-ray disc, USB storage device, removable hard disk) or a fixed recording medium (ROM, RAM, computer equipped hard disk). The computer program recorded on the computer readable medium may be transmitted to other computing device via a network such as internet and installed in the other computing device, thereby being used in the other computing device.

Although the operations are shown in a specific order in the drawings, those skilled in the art will appreciate that many variations and modifications can be made to the preferred embodiments without substantially departing from the principles of the present invention. Therefore, the disclosed preferred embodiments of the invention are used in a generic and descriptive sense only and not for purposes of limitation. The scope of protection of the present invention should be interpreted by the following claims, and all technical ideas within the scope equivalent thereto should be construed as being included in the scope of the technical idea defined by the present invention.

What is claimed is:

1. A light irradiation apparatus comprising:

a body part provided with an internal space capable of containing a user's body region;

a fixing part coupled to the body part and configured to fix the body part to the user's body region in a fixing position;

a base part disposed in the internal space of and configured to be coupled to the body part;

at least one light irradiator coupled to the base part configured to irradiate light on the user's body region;

a position adjustor configured to adjust a position of the at least one light irradiator, the position adjustor comprising one or more actuators; and a computing device configured to control the one or more actuators, wherein the one or more actuators is configured to adjust the position of the at least one light irradiator so that the position of the at least one light irradiator corresponds to a location of the user's body region on which the light is irradiated, wherein the one or more actuators comprise a first actuator configured to adjust a distance between the base part and the user's body region by moving the base part forward toward and backward from the user's body region, wherein the first actuator is configured to adjust the distance between the base part and the user's body region based on occurrence of contact between the base part and the user's body region, and the first actuator is configured to determine the occurrence of the contact between the base part and the user's body region when a contact pressure between the base part and the user's body region is over a first threshold value, wherein the first actuator is configured to tilt the base part disposed in the internal space of the body part, while retaining the body part fixed to the user's body region in the fixing position, based on scanning data for the user's body region, wherein the computing device comprises:

a memory storing a computer program; and a processor, when executing the computer program, configured to obtain a normal vector of the user's body region based on the scanning data, wherein the user's body region is the user's head and the base part has a predetermined axis, wherein the first actuator is configured to operate in multiple modes, including a basic mode and a head top mode, wherein the first actuator is configured to, in the basic mode, tilt the base part disposed in the internal space of the body part such that the predetermined axis of the base part becomes parallel to the normal vector of the user's body region, while retaining the body part fixed to the user's body region in the fixing position, in the head top mode, tilt the base part disposed in the internal space of the body part such that the predetermined axis of the base part forms a predetermined angle with the normal vector of the user's body region, while retaining the body part fixed to the user's body region in the fixing position.

2. The light irradiation apparatus according to claim 1, wherein the first actuator is configured to tilt the base part to an angle corresponding to a predetermined mode.

3. The light irradiation apparatus according to claim 1, wherein the first actuator is configured to move the base part forward toward the user's body region and then move the base part backward from the user's body region in response to the contact between the base part and the user's body region.

4. The light irradiation apparatus according to claim 1, wherein the base part is configured to move to a first position by means of the first actuator, to move to a second position if no contact with the user's body region occurs until moving to the first position, and to move back to the first position after moving to the second position, and the light irradiation apparatus is configured to turn off if no contact between the base part and the user's body region occurs until the base part moves back to the first position.

5. The light irradiation apparatus according to claim 1, wherein the one or more actuators comprise a second actuator configured to adjust a distance between the at least one light irradiator and the user's body region.

6. The light irradiation apparatus according to claim 5, wherein the at least one light irradiator comprises a first light irradiator, and the second actuator is configured to move the first light irradiator forward toward the user's body region and then to move the first light irradiator backward from the user's body region by a first distance in response to a contact between the first light irradiator and the user's body region.

7. The light irradiation apparatus according to claim 6, wherein the computing device is configured to determine that the contact between the first light irradiator and the user's body region occurs if a contact pressure between the first light irradiator and the user's body region is over a second threshold value.

8. The light irradiation apparatus according to claim 6, wherein the at least one light irradiator further comprises a second light irradiator, and the second actuator is configured to move the second light irradiator forward toward the user's body region and then to move the second light irradiator backward from the user's body region by the first distance in response to a contact between the second light irradiator and the user's body region, and the second actuator is configured to maintain, in a state where the first light irradiator and the second light irradiator move backward from the user's body region by the first distance, a distance between a distal end of the first light irradiator and the base part to be different from a distance between a distal end of the second light irradiator and the base part.

9. The light irradiation apparatus according to claim 8, wherein the first light irradiator and the second light irradiator are configured to irradiate the light on the user's body region in a state of moving backward from the user's body region by the first distance.

10. The light irradiation apparatus according to claim 5, wherein the at least one light irradiator is configured to move to a first position by means of the second actuator, to move to a second position if it is detected that no contact with the user's body region occurs until moving to the first position, and to move back to the first position after moving to the second position, and the light irradiation apparatus is configured to turn off if it is detected that no contact with the user's body region occurs until moving back to the first position.

11. The light irradiation apparatus according to claim 1, wherein the at least one light irradiator is configured to change intensity of the light irradiated on the user's body region from the at least one light irradiator based on the scanning data for the user's body region.

12. The light irradiation apparatus according to claim 5, further comprising a third actuator controlled by the computing device and configured to allow the fixing part to come into contact with the user's body region, the third actuator being configured to move the fixing part toward the user's body region and then to stop the movement of the fixing part in response to contact between the fixing part and the user's body region.

13. A method for controlling a light irradiation apparatus comprising a body part provided with an internal space capable of containing a target object and a base part disposed in the internal space of and coupled to the body part, wherein the target object is in a shape of a human's head and the base part has a predetermined axis, the method comprising:

fixing the body part to the target object in a fixing position;

adjusting, by an actuator, a distance between the base part and the target object by moving the base part forward toward and backward from the target object;

determining an operation mode from among multiple predetermined modes, including a basic mode and a head top mode;

obtaining a normal vector of the target object based on scanning data for the target object;

tilting the base part while retaining the body part fixed to the target object in the fixing position based on the scanning data for the target object;

adjusting a position of at least one light irradiator coupled to the base part; and irradiating light on at least one portions of the target object from the at least one light irradiator, wherein adjusting the position of the at least one light irradiator performed so that the position of the at least one light irradiator corresponds to a location of the at least one portions of the target object on which the light is irradiated, wherein the distance between the base part and the target object is adjusted based on occurrence of contact between the base part and the target object, and the occurrence of the contact between the base part and the target object is determined when a contact pressure between the base part and the target object is over a first threshold value, wherein tilting the base part comprises:

in response to determining that the operation mode is the basic mode, tilting the base part disposed in the internal space of the body part such that the predetermined axis of the base part becomes parallel to the normal vector of the target object, while retaining the body part fixed to the target object in the fixing position, in response to determining that the operation mode is the head top mode, tilting the base part disposed in the internal space of the body part such that the predetermined axis of the base part forms a predetermined angle with the normal vector of the target object, while retaining the body part fixed to the target object in the fixing position.

* * * * *